US00PP24533P3

(12) United States Plant Patent
Ferguson et al.

(10) Patent No.: US PP24,533 P3
(45) Date of Patent: Jun. 10, 2014

(54) STRAWBERRY PLANT NAMED 'DRISSTRAWTHIRTYTHREE'

(50) Latin Name: *Fragaria×ananassa*
Varietal Denomination: DrisStrawThirtyThree

(75) Inventors: Michael D. Ferguson, Moorpark, CA (US); Matthias D. Vitten, Aptos, CA (US); Carlos D. Fear, West Malling (GB)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 101 days.

(21) Appl. No.: 13/573,325

(22) Filed: Sep. 11, 2012

(65) Prior Publication Data
US 2014/0075619 P1 Mar. 13, 2014

(51) Int. Cl.
*A01H 5/00* (2006.01)

(52) U.S. Cl.
USPC ..... Plt./208; Plt./209

(58) Field of Classification Search
USPC ..... Plt./208, 209
See application file for complete search history.

*Primary Examiner* — Susan McCormick Ewoldt
(74) *Attorney, Agent, or Firm* — Jondle Plant Sciences Division of Swanson & Bratschun, L.L.C.

(57) ABSTRACT

A new and distinct variety of strawberry plant named 'DrisStrawThirtyThree' particularly characterized by large, orange-red colored, very glossy fruit with sweet flavor is disclosed.

1 Drawing Sheet

Genus and species: *Fragaria×ananassa.*
Variety denomination: 'DrisStrawThirtyThree'.

BACKGROUND OF THE NEW PLANT

The present invention relates to a new and distinct strawberry variety designated 'DrisStrawThirtyThree' and botanically known as *Fragaria×ananassa*. This new strawberry variety was discovered in Ventura, Calif. in February 2008 and originated from a cross between the proprietary female parent '160M 77' (unpatented) and the proprietary male parent 'DrisStrawSixteen' (U.S. Plant Pat. No. 22,247). A single plant was selected for asexual propagation via tissue culture and vegetative cuttings in Shasta County, Calif.

'DrisStrawThirtyThree' underwent further testing in Avitorejo, Spain for two years (2011-2012). The present invention has been found to retain its distinctive characteristics through successive asexual propagations via stolons and tissue culture.

Plant Breeder's Rights for this variety have not been applied for. 'DrisStrawThirtyThree' has not been made publicly available or sold more than one year prior to the filing date of this application.

SUMMARY OF THE INVENTION

The following are the most outstanding and distinguishing characteristics of this new cultivar when grown under normal horticultural practices in Avitorejo, Spain.

1. Large fruit;
2. Orange-red colored fruit; and
3. Very glossy fruit with sweet flavor.

DESCRIPTION OF THE PHOTOGRAPH

The accompanying color photograph shows typical specimens of the new variety at various stages of development. The colors shown are as true as can be reasonably obtained by conventional photographic procedures. The photograph is of whole plants approximately four to five-months-old and shows leaves, flowers, and fruit at various stages of development.

DESCRIPTION OF THE NEW VARIETY

The following detailed descriptions set forth the distinctive characteristics of 'DrisStrawThirtyThree'. The data which define these characteristics is based on observations taken in Avitorejo, Spain from 2011 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyThree' has not been observed under all possible environmental conditions. The botanical description of 'DrisStrawThirtyThree' was taken from four to five-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:
- *Species.*—*Fragaria×ananassa.*
- *Common name.*—Strawberry.
- *Denomination.*—'DrisStrawThirtyThree'.

Parentage:
- *Female parent.*—The proprietary variety '160M 77' (unpatented).
- *Male parent.*—The proprietary variety 'DrisStrawSixteen' (U.S. Plant Pat. No. 22,247).

Plant:
*Height*.—20.4 cm.
*Diameter*.—38.4 cm.
*Number of crowns/plant*.—3.
*Habit*.—Globose — semi-upright.
*Density of individual plant*.—Medium.
*Vigor* (*health and hardiness of plant*).—Weak.

Terminal leaflets:
*Size*.—Small. Length: 7.46 cm. Width: 6.34 cm. Length/width ratio: 1.2 (Longer than broad).
*Number of teeth/terminal leaflet*.—18.
*Shape of teeth*.—Rounded to crenate.
*Color*.—Upper surface: RHS N137A (Dark green). Lower surface: RHS 138B (Medium green).
*Shape in cross section*.—Slightly concave.
*Blistering*.—Medium.
*Glossiness*.—Medium.
*Number of leaflets*.—Three only.
*Shape*.—Orbicular.
*Base shape*.—Acute.
*Apex descriptor*.—Rounded.
*Variegation*.—Absent.
*Margin*.—Serrate.
*Margin profile*.—Cupped.

Petiole:
*Length*.—Short; 12.1 cm.
*Diameter*.—4.22 mm.
*Pubescence*.—Medium.
*Pose of hairs*.—Slightly upwards.
*Color*.—RHS 144B (Medium yellow-green).
*Bract frequency*.—2.

Petiolule:
*Length*.—9.41 mm.
*Diameter*.—1.71 mm.
*Color*.—RHS 144B (Medium yellow-green).

Stipule:
*Length*.—3.1 cm.
*Width*.—8.96 mm.
*Pubescence*.—Dense.
*Stipule anthocyanin coloration*.—Weak; RHS 144B (Medium yellow-green).

Stolon:
*Number*.—Many.
*Average number of daughter plants per plant*.—25.
*Thickness*.—Thick.
*Pubescence*.—Medium.

Inflorescence:
*Position relative to foliage*.—Above.
*Number of flowers*.—Medium.
*Time of flowering* (*50% of plants at first flower*).—Early.
*Flower size*.—Small.
*Diameter*.—32.81 mm.
*Petals*.—Shape: Orbicular. Apex: Rounded. Base: Concavo — convex. Margin: Entire. Spacing: Overlapping. Length: 15.22 mm. Width: 15.13 mm. Length/width ratio: 1.0 (As long as broad). Petal number per flower: 6. Color (upper surface): RHS 155C (White).
*Calyx*.—Diameter: 49.86 mm. Diameter relative to corolla: Same size. Inner calyx diameter relative to outer: Same size. Insertion of calyx: In a basin — inserted. Pose of calyx segments: Spreading to outwards. Size of calyx in relation to fruit: Slightly larger. Adherence of calyx: Strong.
*Sepal*.—Shape: Elliptical. Apex: Truncate. Margin: Serrate. Length: 22.75 mm. Width: 10.49 mm. Sepal number per flower: 12.
*Receptacle color*.—RHS N144D (Light yellow-green).
*Stamen*.—Present. Anther color: RHS 12A (Medium yellow).
*Pedicel*.—Attitude of hairs: Outwards — horizontal.

Fruiting truss:
*Length*.—Long; 26.9 cm.
*Diameter at base of truss*.—4.21 mm.
*Number of berries per fruiting truss*.—2.
*Attitude at first picking*.—Semi-erect.
*Color at base of truss*.—RHS N144D (Light yellow-green).

Fruit:
*Relative fruit size*.—Large.
*Length*.—48.01 mm.
*Width*.—40.14 mm.
*Length/width ratio*.—1.2 (Longer than broad).
*Fruit hollow length*.—13.63 mm.
*Fruit hollow width*.—5.15 mm.
*Fruit hollow length/width ratio*.—2.6.
*Fruit hollow center* (*cavity*).—Small.
*Weight* (*per individual berry*).—24.0 g.
*Predominant fruit shape*.—Conical.
*Difference in shape between primary and secondary fruits*.—None or very slight.
*Evenness of fruit surface*.—Even or very slightly uneven.
*Fruit skin color*.—RHS N34A (Medium orange-red).
*Evenness of fruit color*.—Even or very slightly uneven.
*Fruit glossiness*.—Strong.
*Achenes*.—Insertion of achenes: Below surface. Coloration (sunward side of berry): RHS 144B (Medium yellow-green). Coloration (shaded side of berry): RHS 144A (Medium yellow-green). Number per berry: 328.6. Weight (weight of achenes divided by total # seed): 0.00061 g. Width of band without achenes: Absent or very narrow.
*Firmness of flesh* (*when fully ripe*).—Firm.
*Color of flesh* (*excluding core*).—RHS N30C (Medium orange-red).
*Color of core*.—RHS N30B (Medium orange-red).
*Evenness of flesh color*.—Even.
*Distribution of flesh color*.—Only marginal.
*Sweetness*.—Strong.
*Acidity*.—Weak.
*Texture when tasted*.—Medium.
*Type of bearing*.—Not everbearing — not remontant.
*Grams of fruit/plant*.—1322.3 g.
*Harvest interval*.—Late December to late May.
*Harvest maturity*.—Early.

Disease and pest resistance:
*Tetranychus urticae*.—Moderately resistant.
*Botrytis fruit rot*.—Moderately susceptible.
*Powdery mildew*.—Susceptible.
*Aphis* spp. (*Aphids*).—Resistant.

Reaction to stress:
*Drought*.—Moderately susceptible.
*High temperatures*.—Moderately susceptible.
*Wind*.—Moderately resistant.

COMPARISON WITH PARENTAL AND COMMERCIAL VARIETIES

When 'DrisStrawThirtyThree' is compared to the female parent plant '160M 77' (unpatented), 'DrisStrawThirtyThree' is more vigorous, has less glossy leaves, and has less rain tolerance than '160M 77'.

When 'DrisStrawThirtyThree' is compared to the male parent plant 'DrisStrawSixteen' (U.S. Plant Pat. No. 22,247), 'DrisStrawThirtyThree' has medium leaf blistering, a cupped terminal leaflet margin profile, and many stolons, whereas DrisStrawSixteen has strong leaf blistering, a revolute terminal leaflet margin profile, and few stolons. Additionally, 'DrisStrawThirtyThree' has berries with a small size hollow center and strong sweetness, whereas 'DrisStrawSixteen' has berries with a medium size hollow center and medium sweetness.

When 'DrisStrawThirtyThree' is compared to the commercial variety 'DrisStrawEight' (U.S. Plant Pat. No. 20,735), 'DrisStrawThirtyThree' has 3 crowns per plant, medium glossy leaves, and many stolons, whereas 'DrisStrawEight' has 2 crowns per plant, weakly glossy leaves, and a medium number of stolons. Additionally, 'DrisStrawThirtyThree' has small size flowers and an absent or very narrow band without achenes, whereas 'DrisStrawEight' has medium size flowers and a broad band without achenes.

We claim:

1. A new and distinct variety of strawberry plant named 'DrisStrawThirtyThree' as described and shown herein.

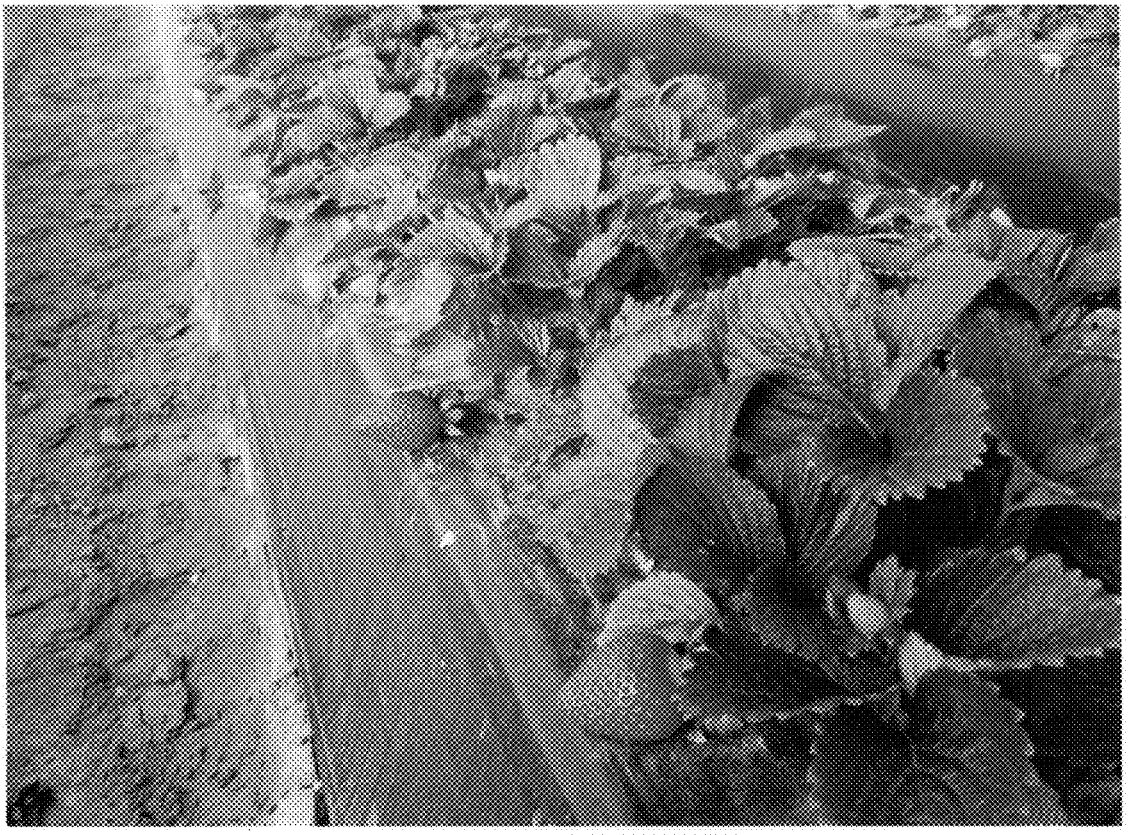

* * * * *